(12) United States Patent
Maeda et al.

(10) Patent No.: US 6,587,208 B2
(45) Date of Patent: Jul. 1, 2003

(54) OPTICAL SYSTEM FOR MEASURING DIAMETER, DISTRIBUTION AND SO FORTH OF MICRO BUBBLES AND MICRO LIQUID DROP

(75) Inventors: Masanobu Maeda, Yokohama (JP); Tatsuya Kawaguchi, Yokohama (JP)

(73) Assignee: Keio University, Tokyo (JP)

( * ) Notice: Subject to any disclaimer, the term of this patent is extended or adjusted under 35 U.S.C. 154(b) by 95 days.

(21) Appl. No.: 09/926,112

(22) PCT Filed: Dec. 21, 2000

(86) PCT No.: PCT/JP00/09082

§ 371 (c)(1),
(2), (4) Date: Sep. 4, 2001

(87) PCT Pub. No.: WO01/50111

PCT Pub. Date: Jul. 12, 2001

(65) Prior Publication Data

US 2002/0159070 A1 Oct. 31, 2002

(30) Foreign Application Priority Data

Jan. 7, 2000 (JP) ......................................... 2000-001694

(51) Int. Cl.[7] .................................................. G01B 9/02
(52) U.S. Cl. ..................................................... 356/496
(58) Field of Search ................................ 356/496, 335, 356/336, 635

(56) References Cited

U.S. PATENT DOCUMENTS 4,334,779 A * 6/1982 Domey et al. .............. 356/496
5,784,160 A * 7/1998 Naqwi ........................ 356/496

* cited by examiner

Primary Examiner—Samuel A. Turner
Assistant Examiner—Michael A. Lyons
(74) Attorney, Agent, or Firm—Armstrong, Westerman & Hattori, LLP

(57) ABSTRACT

The present invention expands a method of measuring the diameter, spatial distribution and so forth of micro liquid droplets by measuring the diameter of each out-of-focus image obtained by defocusing and the number of interference fringes in the out-of-focus image into a measuring method for micro gas bubbles and allows the method to be applied to a case where the spatial distribution density of micro liquid droplets and micro gas bubbles is high. A sheet-shaped parallel laser beam (2) is applied to a liquid space in which micro gas bubbles (10) are floating, and out-of-focus images of micro gas bubbles (10) irradiated with the laser beam (2) are captured at a defocus plane (8) through an objective lens (6) from a lateral direction which is at an angle θ to the direction of travel of the laser beam. The number of interference fringes (9) in an out-of-focus image (10") corresponding to a micro gas bubble (10) is measured, and the diameter of the micro gas bubble (10) is determined according to equation (4).

16 Claims, 12 Drawing Sheets

FIG. 10
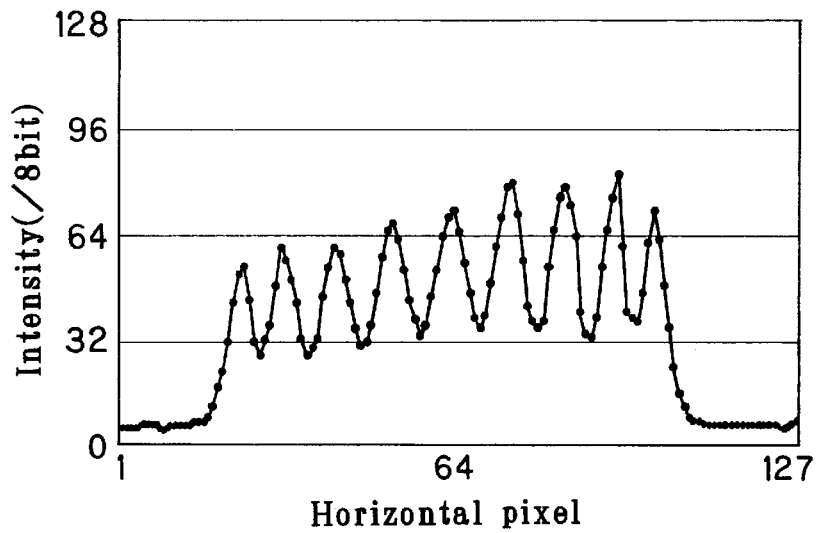
(a)
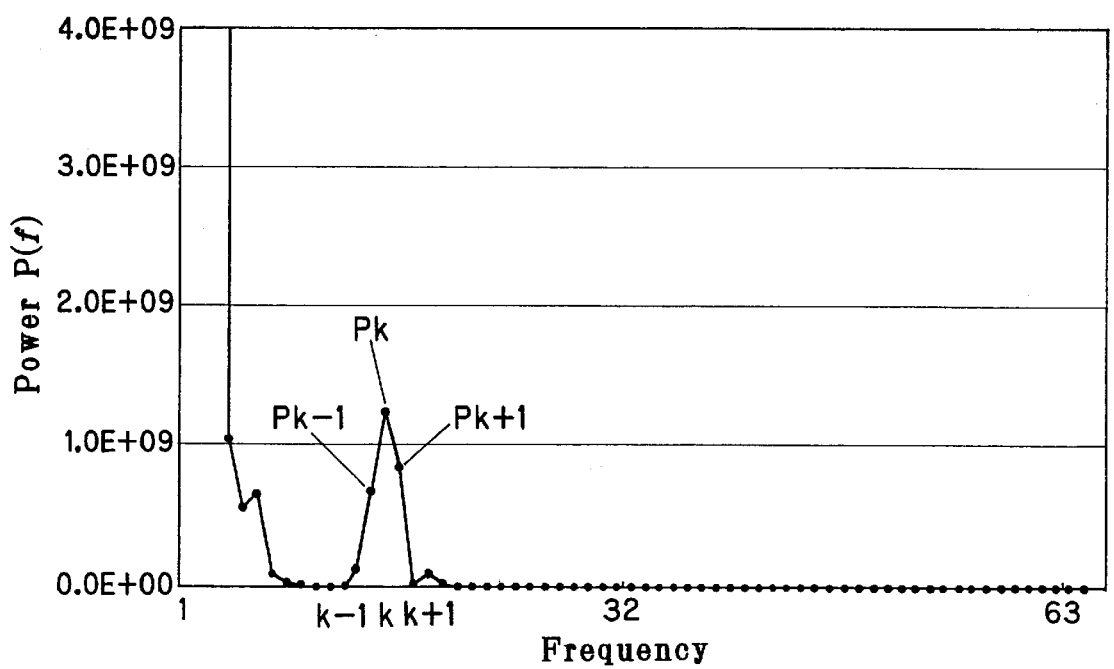
(b)

FIG. 12
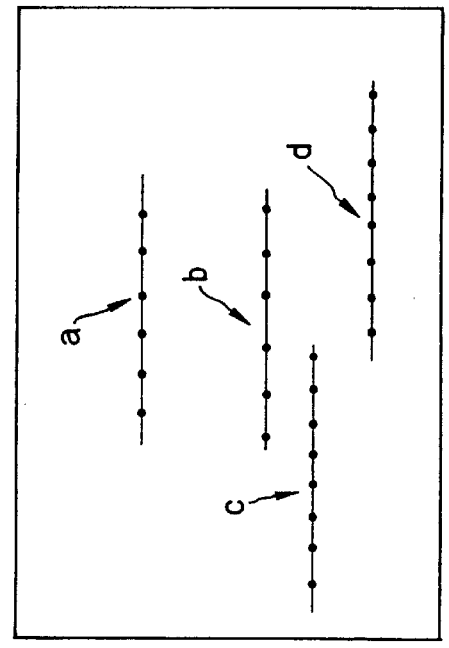
(b)
A'
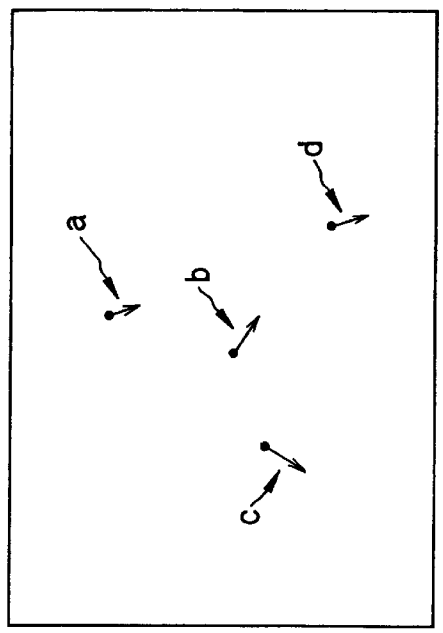
(c)
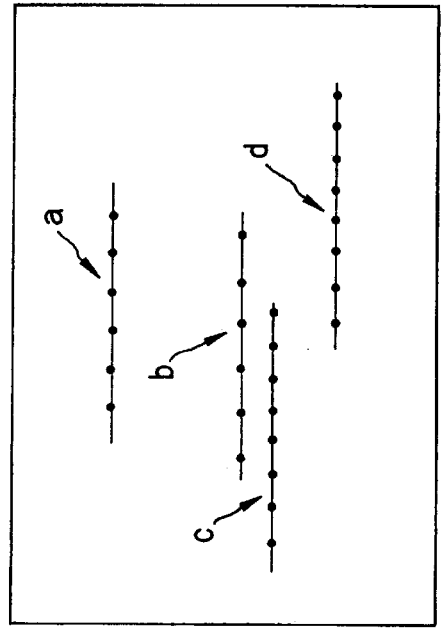
(a)
A

OPTICAL SYSTEM FOR MEASURING DIAMETER, DISTRIBUTION AND SO FORTH OF MICRO BUBBLES AND MICRO LIQUID DROP

TECHNICAL FIELD

The present invention relates to a method and apparatus, together with an optical system, for measuring the diameter, distribution and so forth of micro liquid droplets and micro gas bubbles. More particularly, the present invention relates to a method and apparatus, together with an optical system, for simultaneously measuring the diameter and distribution of micro liquid droplets and micro gas bubbles distributed in a space by an interferometric method.

BACKGROUND ART

A method of accurately measuring the distribution and diameters of micro liquid droplets of fuel injected into an engine, for example, is demanded. Similarly, a method of accurately measuring the distribution and diameters of micro liquid droplets sprayed in the air is demanded to design a nozzle used in the spray dry method, for example. Further, a method of accurately measuring the diameter and distribution of gas bubbles, together with changes thereof, is demanded in the study of absorption of $CO_2$ in air bubbles into the sea and the behavior of gas bubbles in beer and wine.

Thus, there is a strong demand in various fields for a method and apparatus for accurately measuring the diameter and distribution of micro liquid droplets and gas bubbles in the state of being present in a space.

Regarding micro liquid droplets, there has heretofore been a method in which micro liquid droplets distributed in a space are photographed and the photograph is analyzed. This method involves a problem in terms of measurement accuracy because the photograph may be out of focus or may become unsharp for other reasons. The method further suffers from the problem that real-time processing cannot be performed. A method in which the photograph is taken with a CCD camera is also known. This method also suffers from the problem in terms of measurement accuracy and the problem that real-time processing cannot be performed. Further, the method involves the problem that a great deal of time is required for analysis. A holographic technique and a method using a CCD camera for imaging are also known. However, these methods similarly involve the problem in terms of measurement accuracy and the problems that real-time processing cannot be performed and a great deal of time is required for analysis. There is also known a method in which the shadows of micro liquid droplets are captured directly with a CCD camera in order to obtain real-time capability. With this method, however, it is difficult to measure small particles because of the influence of diffraction. The method further involves the problem that it is difficult to measure the diameter of micro liquid droplets in limited three-dimensional positions.

In addition, there has heretofore been known a method in which a plurality of particles are simultaneously measured by specifying positions in a three-dimensional space with a method known as LDV, PDA, PDPA, etc. With this method, two laser beams are crossed in the air to form spatial interference fringes, and light scattered from liquid droplets crossing the interference fringes is observed with the same measurement volume from a plurality of different points. The diameters of the micro liquid droplets are measured from the phase differences between the measurement signals. In this case, because the diameter of each individual particle passing through the interference fringe area is measured, the method suffers from the problem that measurement in the space surrounding the interference fringe area cannot simultaneously be performed. The measurement accuracy is also unsatisfactory.

Under these circumstances, a method has been proposed (SAE Paper no. 950457, 960830) in which a sheet-shaped parallel laser beam is applied to a measurement space, and out-of-focus images of micro liquid droplets irradiated with the laser beam are captured. In the out-of-focus image corresponding to each micro liquid droplet, interference fringes are present, and there is a fixed relationship between the number of interference fringes present in the out-of-focus image and the diameter of the micro liquid droplet. Accordingly, the diameter of the micro liquid droplet can be measured by measuring the number of interference fringes. It is also possible to measure the spatial distribution of the micro liquid droplets.

With the above-described method of measuring the diameter and spatial distribution of micro liquid droplets by measuring the number of interference fringes in each out-of-focus image, the applicable field is limited to micro liquid droplets. The method has not heretofore been applied to micro gas bubbles.

Further, the above-described method involves the problem that when the spatial distribution density of micro liquid droplets is high, out-of-focus images overlap each other because they are circular and occupy large areas. Therefore, it is difficult to measure the diameters of the micro liquid droplets separately.

DISCLOSURE OF THE INVENTION

The present invention was made in view of the above-described problems with the prior art, and an object of the present invention is to expand the method of measuring the diameter and spatial distribution of micro liquid droplets by measuring the diameter of each out-of-focus image obtained by defocusing and the number of interference fringes in the out-of-focus image into a method of measuring the diameter and spatial distribution of micro gas bubbles, and to provide a measuring optical system that allows the method to be applied to a case where the spatial distribution density of micro liquid droplets and micro gas bubbles is high.

Another object of the present invention is to provide a method and apparatus for determining the position, diameter and velocity of micro liquid droplets and micro gas bubbles from the analysis of out-of-focus images.

A method of measuring the diameter, distribution and so forth of micro gas bubbles according to the present invention, which is provided to attain the above-described objects, is a method wherein a sheet-shaped parallel laser beam is applied to a liquid space in which micro gas bubbles are floating, and out-of-focus images of micro gas bubbles irradiated with the laser beam are captured from a lateral direction which is at an angle θ to the direction of travel of the laser beam. The number N of interference fringes in the out-of-focus image corresponding to each micro gas bubble is measured, and the diameter D of the micro gas bubble is determined from the following relationship:

$$D=(2\lambda N/n\alpha)[\cos(\theta/2)-\sin(\theta/2)+\sqrt{\{n^2+1-2n\cos(\theta/2)\}}]^{-1} \qquad (4)$$

where λ is the wavelength of the laser beam; α is the angle subtended at the micro gas bubble by an objective lens used to capture the image of the micro gas bubble; and n is the relative index of refraction of a liquid in which the micro gas bubble is present.

Another method of measuring the diameter, distribution and so forth of micro gas bubbles and micro liquid droplets according to the present invention is a method wherein a sheet-shaped parallel laser beam is applied to a space in which micro gas bubbles or micro liquid droplets are floating; out-of-focus images of micro gas bubbles or micro liquid droplets irradiated with the laser beam are captured from a lateral direction which is at a predetermined angle to the direction of travel of the laser beam; and the numbers of interference fringes in the respective out-of-focus images corresponding to the micro gas bubbles or the micro liquid droplets are measured to determine the diameters and distribution of the micro gas bubbles or the micro liquid droplets.

The method is characterized in that the out-of-focus images are captured with an imaging optical system at an imaging plane where the images are out of focus in a direction parallel to a plane containing the direction of travel of the sheet-shaped parallel laser beam and an optical axis of the imaging optical system and where the images are substantially in focus in a direction perpendicular to the plane.

In this case, it is desirable that the spacing of interference fringes on the imaging plane be adjustable by adjusting the defocus condition of the out-of-focus images.

The arrangement may be such that the sheet-shaped parallel laser beam is moved in parallel to a direction perpendicular to the plane of the sheet-shaped parallel laser beam with respect to the space in which micro gas bubbles or micro liquid droplets are floating, and the out-of-focus images are captured in synchronism with the movement of the sheet-shaped parallel laser beam.

Another method of measuring the diameter, distribution and so forth of micro gas bubbles and micro liquid droplets according to the present invention is a method wherein a sheet-shaped parallel laser beam is applied to a space in which micro gas bubbles or micro liquid droplets are floating, and linear out-of-focus images of micro gas bubbles or micro liquid droplets irradiated with the laser beam are captured from a lateral direction which is at a predetermined angle to the direction of travel of the laser beam with an imaging optical system at an imaging plane where the images are out of focus in a direction parallel to a plane containing the direction of travel of the laser beam and an optical axis of the imaging optical system and where the images are substantially in focus in a direction perpendicular to the plane. The linear out-of-focus images extend in the direction of the plane in correspondence to the micro gas bubbles or the micro liquid droplets. The center of each of the out-of-focus images is determined to thereby determine the center position of the corresponding micro gas bubble or micro liquid droplet.

In this case, it is desirable that the center position be determined from a peak position of a moving average value obtained by taking an average in the range extending from a distance L/2 forward of a specific position to a distance L/2 rearward of the specific position in the longitudinal direction and determining the average to be a value at this position, where L is the length of a linear out-of-focus image, and successively moving the specific position.

Another method of measuring the diameter, distribution and so forth of micro gas bubbles and micro liquid droplets according to the present invention is a method wherein a sheet-shaped parallel laser beam is applied to a space in which micro gas bubbles or micro liquid droplets are floating, and linear out-of-focus images of micro gas bubbles or micro liquid droplets irradiated with the laser beam are captured from a lateral direction which is at a predetermined angle to the direction of travel of the laser beam with an imaging optical system at an imaging plane where the images are out of focus in a direction parallel to a plane containing the direction of travel of the laser beam and an optical axis of the imaging optical system and where the images are substantially in focus in a direction perpendicular to the plane. The linear out-of-focus images extend in the direction of the plane in correspondence to the micro gas bubbles or the micro liquid droplets. Each of the out-of-focus images is subjected to Fourier transform to obtain a frequency, and the obtained frequency is multiplied by the length of the out-of-focus image to obtain the number of interference fringes in the out-of-focus image. The diameter of the micro gas bubble or the micro liquid droplet is determined on the basis of the number of interference fringes.

In this case, it is desirable that discrete Fourier transform be performed as the Fourier transform to obtain a discrete frequency distribution, and function fitting be applied to the discrete frequency distribution to obtain the diameter of the micro gas bubble or the micro liquid droplet.

A further method of measuring the diameter, distribution and so forth of micro gas bubbles and micro liquid droplets according to the present invention is a method wherein a sheet-shaped parallel laser beam is applied to a space in which micro gas bubbles or micro liquid droplets are floating, and two image frames are captured at a micro time interval $\Delta t$, each of which two image frames contains linear out-of-focus images of micro gas bubbles or micro liquid droplets irradiated with the laser beam. The linear out-of-focus images are captured from a lateral direction which is at a predetermined angle to the direction of travel of the laser beam with an imaging optical system at an imaging plane where the images are out of focus in a direction parallel to a plane containing the direction of travel of the laser beam and an optical axis of the imaging optical system and where the images are substantially in focus in a direction perpendicular to the plane. The linear out-of-focus images extend in the direction of the plane in correspondence to the micro gas bubbles or the micro liquid droplets. Cross correlation between the two captured image frames is calculated for each linear out-of-focus image in the two captured image frames to obtain the displacement $\Delta s_i$ of each linear out-of-focus image, and the velocity $u_i$ of each micro gas bubble or micro liquid droplet is determined from the following relationship:

$$u_i = \Delta s_i / \Delta t \quad (6)$$

In this case, it is desirable to remove a high-frequency component corresponding to interference fringes in the linear out-of-focus image when calculating cross correlation between the two captured image frames.

A still further method of measuring the diameter, distribution and so forth of micro gas bubbles and micro liquid droplets according to the present invention is a method wherein a sheet-shaped parallel laser beam is applied to a space in which micro gas bubbles or micro liquid droplets are floating, and linear out-of-focus images of micro gas bubbles or micro liquid droplets irradiated with the laser beam are captured from a lateral direction which is at a predetermined angle to the direction of travel of the laser beam with an imaging optical system at an imaging plane where the images are out of focus in a direction parallel to a plane containing the direction of travel of the laser beam and an optical axis of the imaging optical system and where the images are substantially in focus in a direction perpendicular to the plane. The linear out-of-focus images extend in the direction of the plane in correspondence to the micro gas bubbles or the micro liquid droplets. The center of each of the out-of-focus images is determined to thereby determine the center position of the corresponding micro gas bubble or micro liquid droplet. Each of the out-of-focus images is subjected to Fourier transform to obtain a frequency, and the obtained frequency is multiplied by the length of the out-of-focus image to obtain the number of interference fringes in the out-of-focus image. The diameter of the micro gas bubble or the micro liquid droplet is determined on the basis of the number of interference fringes. Further, two image frames containing the linear out-of-focus images are captured at a micro time interval $\Delta t$. Cross correlation between the two captured image frames is calculated for each linear out-of-focus image in the two captured image frames to obtain the displacement $\Delta s_i$ of each linear out-of-focus image, and the velocity $u_i$ of each micro gas bubble or micro liquid droplet is determined from the following relationship:

$$u_i = \Delta s_i / \Delta t \tag{6}$$

An apparatus for measuring the diameter, distribution and so forth of micro gas bubbles and micro liquid droplets according to the present invention includes laser beam application means for applying a sheet-shaped parallel laser beam to a space in which micro gas bubbles or micro liquid droplets are floating, and imaging means for capturing linear out-of-focus images of micro gas bubbles or micro liquid droplets irradiated with the laser beam, which is applied by the laser beam application means, from a lateral direction which is at a predetermined angle to the direction of travel of the laser beam with an imaging optical system at an imaging plane where the images are out of focus in a direction parallel to a plane containing the direction of travel of the laser beam and an optical axis of the imaging optical system and where the images are substantially in focus in a direction perpendicular to the plane. The linear out-of-focus images extend in the direction of the plane in correspondence to the micro gas bubbles or the micro liquid droplets. The apparatus further includes center position measuring means for determining the center of each of the out-of-focus images to thereby determine the center position of the corresponding micro gas bubble or micro liquid droplet, and diameter measuring means for subjecting each of the out-of-focus images to Fourier transform to obtain a frequency, multiplying the obtained frequency by the length of the out-of-focus image to obtain the number of interference fringes in the out-of-focus image, and determining the diameter of the micro gas bubble or the micro liquid droplet on the basis of the number of interference fringes. Further, the apparatus includes velocity measuring means for capturing two image frames containing the linear out-of-focus images at a micro time interval $\Delta t$, calculating cross correlation between the two captured image frames for each linear out-of-focus image in the two captured image frames to obtain the displacement $\Delta s_i$ of each linear out-of-focus image, and determining the velocity $u_i$ of each micro gas bubble or micro liquid droplet from the following relationship:

$$u_i = \Delta s_i / \Delta t \tag{6}$$

An optical system for measuring the diameter, distribution and so forth of micro gas bubbles and micro liquid droplets according to the present invention is a measuring optical system wherein a sheet-shaped parallel laser beam is applied to a space in which micro gas bubbles or micro liquid droplets are floating; out-of-focus images of micro gas bubbles or micro liquid droplets irradiated with the laser beam are captured from a lateral direction which is at a predetermined angle to the direction of travel of the laser beam; and the numbers of interference fringes in the respective out-of-focus images corresponding to the micro gas bubbles or the micro liquid droplets are measured to determine the diameters and distribution of the micro gas bubbles or the micro liquid droplets.

The measuring optical system is characterized by including an imaging optical system in which the focal length or the image-side principal plane in a direction parallel to a plane containing the direction of travel of the sheet-shaped parallel laser beam and an optical axis of the imaging optical system and the focal length or the image-side principal plane in a direction perpendicular to the plane containing the optical axis of the imaging optical system are different from each other, and image pickup means placed in an image plane which is in the vicinity of the image-formation plane in the direction perpendicular to the above-described plane and which is off the image-formation plane in the direction parallel to the above-described plane.

In this case, it is desirable that the imaging optical system be an anamorphic optical system comprising a combination of an axially symmetric objective lens and a cylindrical lens.

It is also desirable that at least one of the focal length and the image-side principal plane of the imaging optical system in the direction parallel to the plane be adjustable.

It is also desirable that the imaging optical system have a rectangular aperture elongated in the direction parallel to the plane.

In the present invention, out-of-focus images of micro gas bubbles or micro liquid droplets are captured with an imaging optical system at an imaging plane where the images are out of focus in a direction parallel to a plane containing the direction of travel of a sheet-shaped parallel laser beam and the optical axis of the imaging optical system and where the images are substantially in focus in a direction perpendicular to the plane. Consequently, the out-of-focus image corresponding to each micro gas bubble or micro liquid droplet becomes a one-dimensional image compressed in the direction perpendicular to the plane. Therefore, even when the spatial distribution density of micro gas bubbles and micro liquid droplets is high, the respective out-of-focus images can be separated from each other. Accordingly, the number of interference fringes in each out-of-focus image can be readily counted separately from each other. In addition, it becomes easy to determine the center position of each out-of-focus image to detect the distributed conditions of micro gas bubbles or micro liquid droplets. Even in such a case, the position, diameter and velocity distributions of micro gas bubbles and micro liquid droplets can be measured simultaneously and accurately.

BRIEF DESCRIPTION OF THE DRAWINGS

FIG. 10 is a diagram showing an image signal of an interference fringe image and an example of a power spectrum obtained therefrom by FFT.

FIG. 12 is a diagram for explaining a method of determining the velocity of micro liquid droplets by calculating cross correlation.

BEST MODE FOR CARRYING OUT THE INVENTION

The following is a description of the principles and embodiments of the method and apparatus for measuring the diameter, distribution and so forth of micro liquid droplets and micro gas bubbles and the measuring optical system according to the present invention.

First, the principle of a publicly known method of measuring the diameter and spatial distribution of micro liquid droplets by measuring the number of interference fringes in each out-of-focus image will be described with a view to facilitating understanding.

Figure 3:
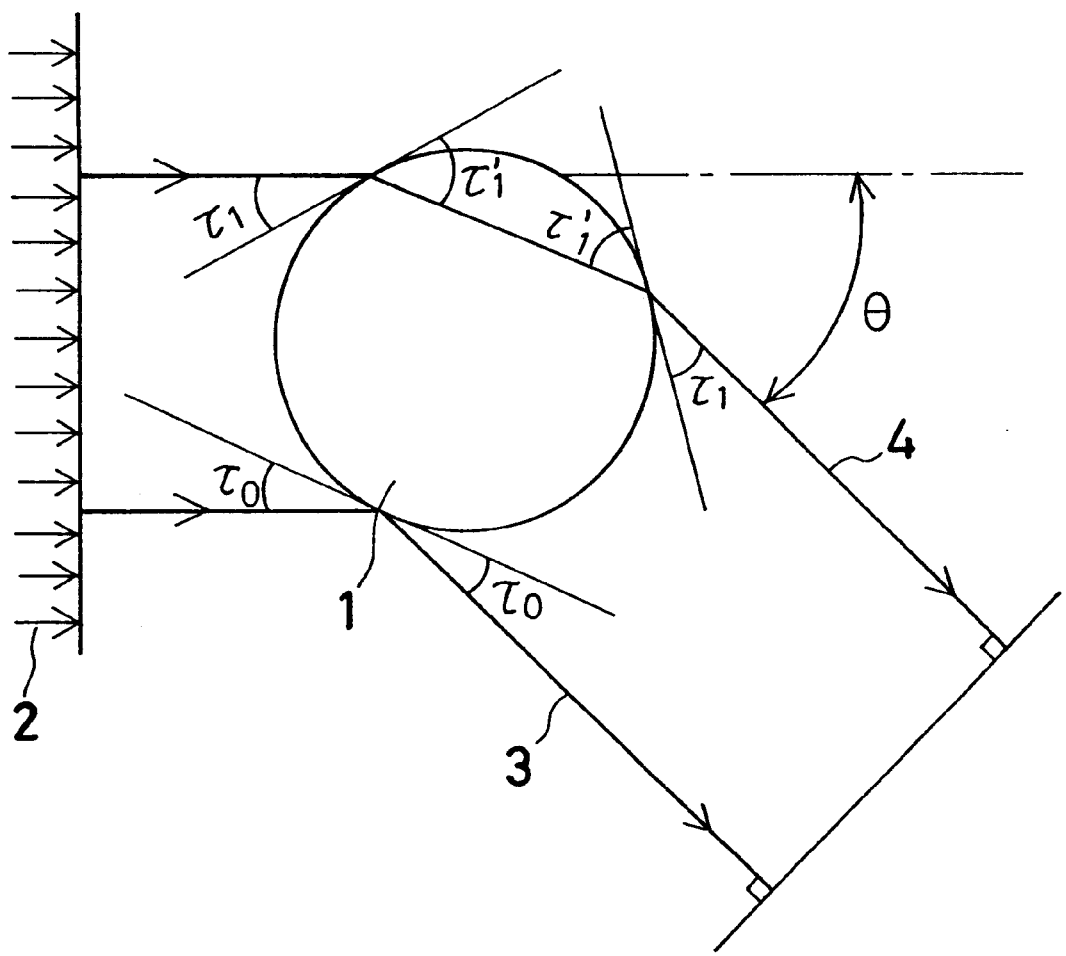
FIG. 3 is a diagram for analyzing light rays passing through a micro liquid droplet floating in the air.

First, as shown in FIG. 3, a plane wave 2 is made incident on a micro liquid droplet 1 of refractive index n floating in the air. At this time, there is a difference in the angle θ measured when twice-refracted light 4 of incident angle (hereinafter, both the incident angle and the refraction angle will be assumed to be angles measured from a tangential plane to the interface) $\tau_1$ and once-reflected light 3 of incident angle $\tau_0$ are parallel to each other and the phase difference therebetween is 2 mπ (m is an integer) and when the phase difference between the refracted light 4 and the reflected light 3 is 2(m+1)π. The angular difference Δθ is given by $$\Delta\theta=(2\lambda/D)[n \sin(\theta/2)+\sqrt{\{n^2+1-2n \cos(\theta/2)\}}+\cos(\theta/2)]^{-1} \qquad (1)$$

where θ is the viewing angle of scattered light from the micro liquid droplet 1 with respect to the illuminating light 2; D is the diameter of the micro liquid droplet 1; and λ is the wavelength of the illuminating light 2.

The meaning of the above is as follows. As shown in FIG. 1(a), scattered light 5 from the micro liquid droplet 1 contains a row of high-intensity portions (interference fringes) produced by interference at a micro angular spacing Δθ, which are centered in the direction of scattering angle θ with respect to the illuminating light 2. When an objective lens (imaging lens) 6 is placed in the path of the scattered light 5 to form an image 1' of the micro liquid droplet 1 on an image plane 7 by the scattered light 5, an out-of-focus image 1" of the micro liquid droplet 1 such as that shown in FIG. 1(b) is obtained on an out-of-focus plane (defocus plane) 8, which is off the image plane 7. The range shown by the dashed lines in FIGS. 1(a) and (b) indicates the range of a bundle of rays incident on the objective lens 6. The external size and shape of the out-of-focus image 1" of the micro liquid droplet 1 obtained on the out-of-focus plane 8 depend on the size of the objective lens 6 and the distance from the image plane 7 to the out-of-focus plane 8 independently of the size of the micro liquid droplet 1. When the external shape of the objective lens 6 is circular, the out-of-focus image 1" of the micro liquid droplet 1 is circular. The number N of interference fringes 9 formed within the circle is determined by the angle α subtended at the micro liquid droplet 1 by the objective lens 6 and the above-described angular difference Δθ.

That is, from the relationship of α=N×Δθ and the above equation (1), the diameter of the micro liquid droplet 1 is given by $$D=(2\lambda N/\alpha)[n \sin(\theta/2)+\sqrt{\{n^2+1-2n \cos(\theta/2)\}}+\cos(\theta/2)]^{-1} \qquad (2)$$

The diameter D of the micro liquid droplet 1 can be obtained by substituting the number N of interference fringes 9 in the out-of-focus image 1" actually observed and measured into equation (2).

As will be clear from FIG. 1(a), when sheet-shaped parallel light extending in a direction perpendicular to the plane of the figure is used as the illuminating light 2 and micro liquid droplets $1_1, 1_2, \ldots$ are present in the path of the light in addition to the micro liquid droplet 1, out-of-focus images $1_1", 1_2", \ldots$ are also obtained on the out-of-focus plane 8 as in the case of the micro liquid droplet 1, and the diameter D can similarly be obtained. The center positions of the out-of-focus images $1_1", 1_2", \ldots$ approximately correspond to the center positions of the images 1', $1_1'$, $1_2', \ldots$ of the micro liquid droplets 1, $1_1, 1_2, \ldots$ on the image plane 7. Therefore, the distribution of the micro liquid droplets and the diameter of each micro liquid droplet can be simultaneously determined from the out-of-focus images $1_1", 1_2", \ldots$ obtained on the out-of-focus plane 8.

The foregoing is the principle of the publicly known method of measuring the diameter and spatial distribution of micro liquid droplets by measuring the number of interference fringes in each out-of-focus image. Let us consider obtaining the distribution and diameter of micro gas bubbles present in a liquid in place of micro liquid droplets.

Figure 2:
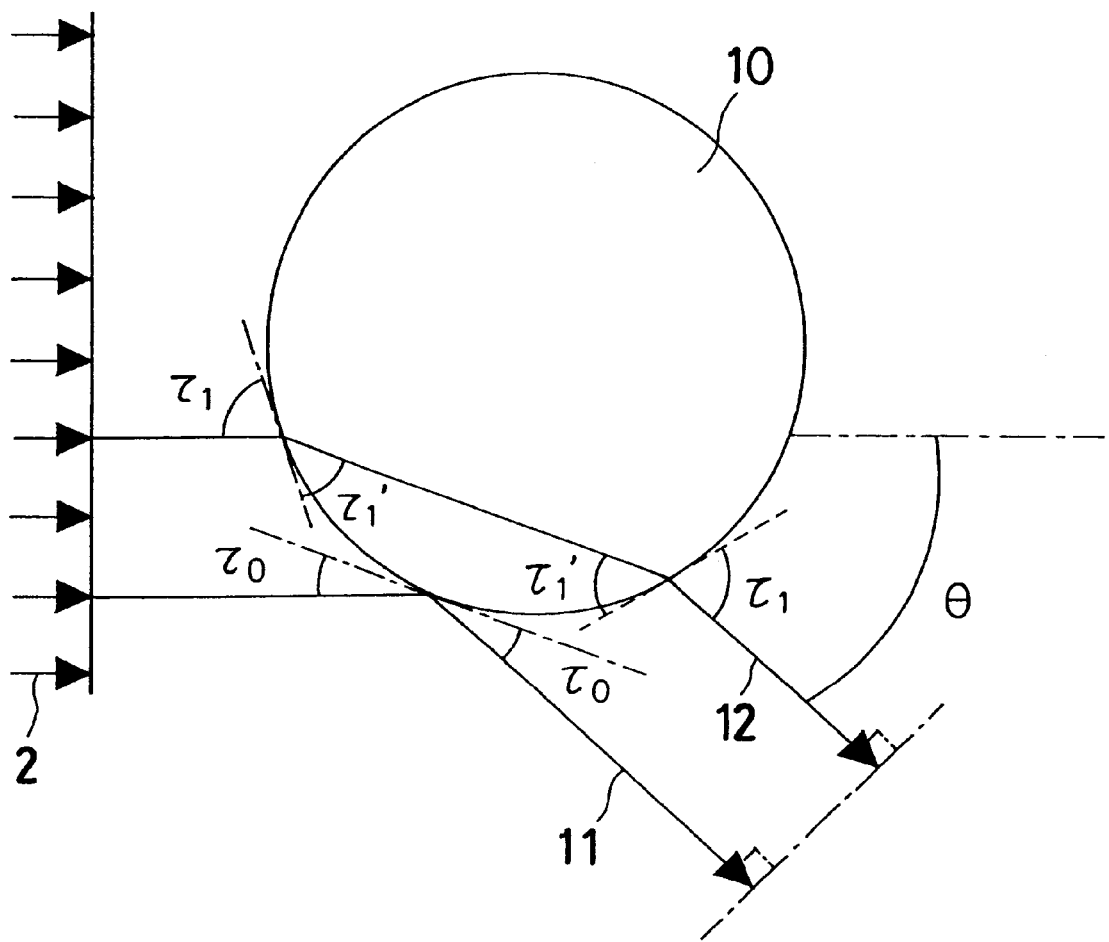
FIG. 2 is a diagram for analyzing light rays passing through a micro gas bubble floating in a liquid.

In FIG. 2, a plane wave 2 is made incident on a micro gas bubble 10 of refractive index 1 floating in a liquid. At this time, there is a difference in the angle θ measured when twice-refracted light 12 of incident angle $\tau_1$ and once-reflected light 11 of incident angle $\tau_0$ are parallel to each other and the phase difference therebetween is 2 mπ (m is an integer) and when the phase difference between the refracted light 12 and the reflected light 11 is 2(m+1)π. The angular difference Δθ is given by $$\Delta\theta=(2\lambda/nD)[\cos(\theta/2)-\sin(\theta/2)+\sqrt{\{n^2+1-2n \cos(\theta/2)\}}]^{-1} \qquad (3)$$

where θ is the viewing angle of scattered light from the micro gas bubble 10 with respect to the illuminating light 2;

D is the diameter of the micro gas bubble 10; and λ is the wavelength of the illuminating light 2.

Figure 1:
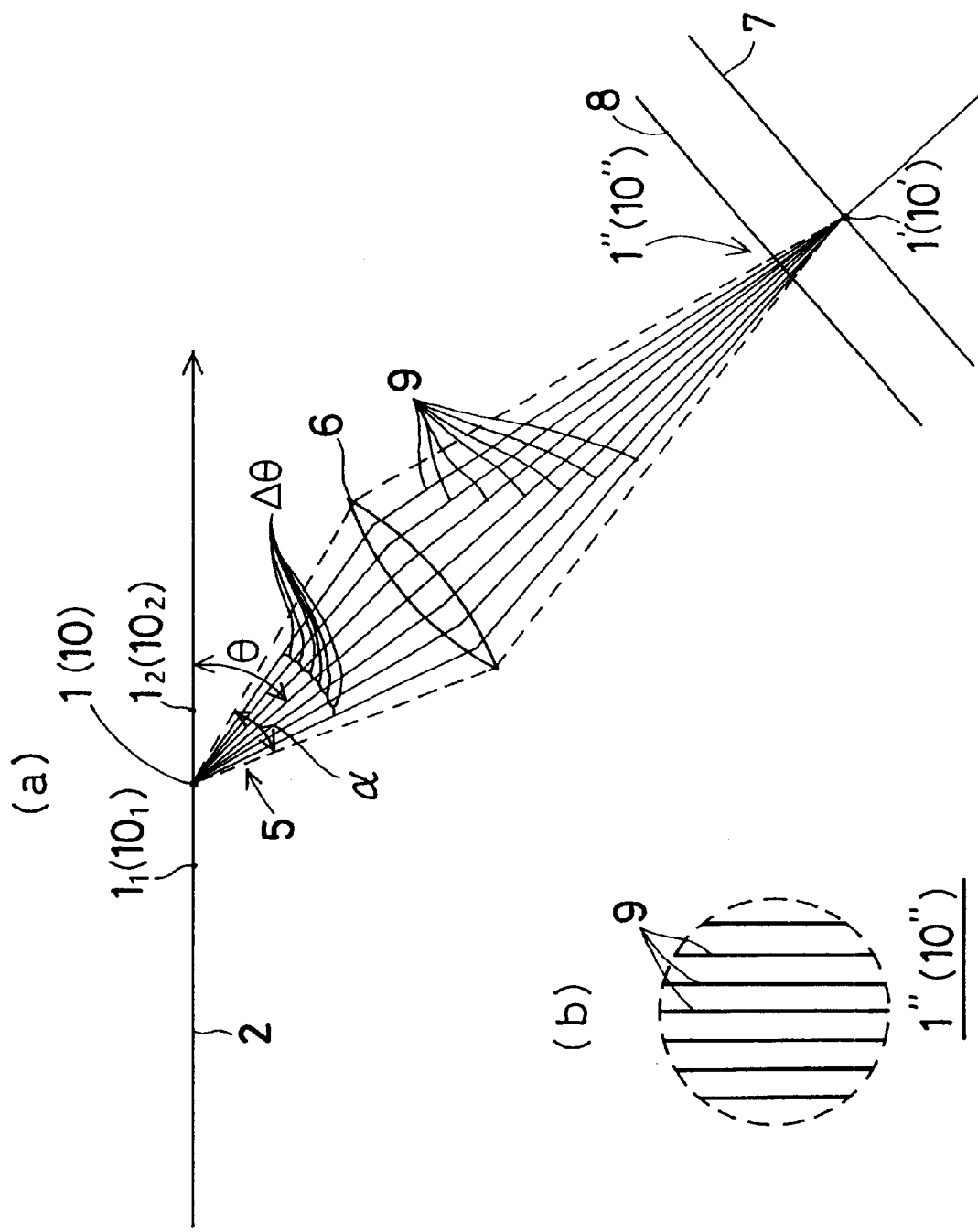
FIG. 1 is a diagram for explaining the principle of the method of measuring the diameter and spatial distribution of micro gas bubbles according to the present invention and the principle of a conventional method of measuring the diameter and spatial distribution of micro liquid droplets and shows an example of an out-of-focus image of a micro gas bubble or a micro liquid droplet.

The meaning of the above is as follows. As shown in FIG. 1(*a*), scattered light 5 from the micro gas bubble 10 contains a row of high-intensity portions (interference fringes) produced by interference at a micro angular spacing Δθ, which are centered in the direction of scattering angle θ with respect to the illuminating light 2. When an objective lens 6 is placed in the path of the scattered light 5 to form an image 10' of the micro gas bubble 10 on an image plane 7 by the scattered light 5, an out-of-focus image 10" of the micro gas bubble 10 such as that shown in FIG. 1(*b*) is obtained on an out-of-focus plane (defocus plane) 8, which is off the image plane 7. The range shown by the dashed lines in FIGS. 1(*a*) and (*b*) indicates the range of a bundle of rays incident on the objective lens 6. The external size and shape of the out-of-focus image 10" of the micro gas bubble 10 obtained on the out-of-focus plane 8 depend on the size of the objective lens 6 and the distance from the image plane 7 to the out-of-focus plane 8 independently of the size of the micro gas bubble 10. When the external shape of the objective lens 6 is circular, the out-of-focus image 10" of the micro gas bubble 10 is circular. The number N of interference fringes 9 formed within the circle is determined by the angle α subtended at the micro gas bubble 10 by the objective lens 6 and the above-described angular difference Δθ.

That is, from the relationship of α=N×Δθ and the above equation (3), the diameter D of the micro gas bubble 10 is given by $$D=(2\lambda N/n\alpha)[\cos(\theta/2)-\sin(\theta/2)+\sqrt{\{n^2+1-2n\cos(\theta/2)\}}]^{-1} \quad (4)$$

The diameter D of the micro gas bubble 10 can be obtained by substituting the number N of interference fringes 9 in the out-of-focus image 10" actually observed and measured into equation (4).

As will be clear from FIG. 1(*a*), when sheet-shaped parallel light extending in a direction perpendicular to the plane of the figure is used as the illuminating light 2 and micro gas bubbles $10_1$, $10_2$, ... are present in the path of the light in addition to the micro gas bubble 10, out-of-focus images $10_1''$, $10_2''$, ... are also obtained on the out-of-focus plane 8 as in the case of the micro gas bubble 10, and the diameter D can similarly be obtained. The center positions of the out-of-focus images $10_1''$, $01_2''$, ... approximately correspond to the center positions of the images 10', $10_1'$, $10_2'$, ... of the micro gas bubbles 10, $10_1$, $10_2$, ... on the image plane 7. Therefore, the distribution of the micro gas bubbles and the diameter of each micro gas bubble can be simultaneously determined from the out-of-focus images $10_1''$, $10_2''$, ... obtained on the out-of-focus plane 8.

It will be understood from the above discussion that in the case of micro gas bubbles also, when a sheet-shaped parallel laser beam is applied to a measurement space to capture out-of-focus images of micro gas bubbles irradiated with the laser beam, interference fringes are present in the out-of-focus image corresponding to each micro gas bubble, and there is a fixed proportional relationship between the number of interference fringes present in the out-of-focus image and the diameter of the micro gas bubble. Accordingly, it is possible to measure the diameter of the micro gas bubble by measuring the number of interference fringes, and the distribution of the micro gas bubbles can be simultaneously obtained from the distribution of the center positions of the out-of-focus images.

Figure 6:
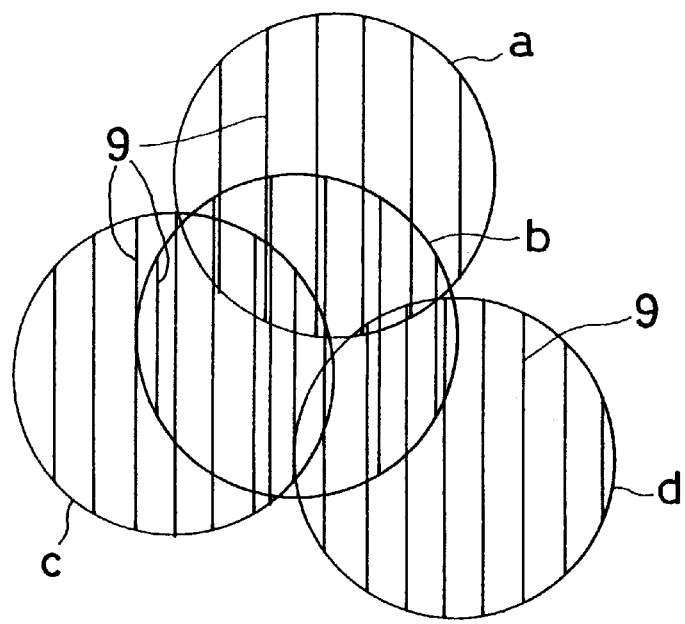
FIG. 6 is a diagram showing an example of out-of-focus images captured with an arrangement as shown in FIG. 1(a).

Incidentally, FIG. 6 shows schematically an example of out-of-focus images captured with an arrangement as shown in FIG. 1(*a*) when the spatial distribution density of micro liquid droplets or micro gas bubbles is high. In the following, we will discuss micro liquid droplets typically because it is understood that micro gas bubbles and micro liquid droplets can be handled similarly except for the difference between equations (4) and (2).

FIG. 6 shows out-of-focus images a, b, c and d of four micro liquid droplets 1 captured at the out-of-focus plane 8 with the arrangement shown in FIG. 1(*a*) in a case where the four micro liquid droplets 1 are present in close proximity to each other in the path of the sheet-shaped parallel illuminating light 2. Because the four micro liquid droplets 1 are too close to each other, the out-of-focus images a, b, c and d with circular outer shapes corresponding to the micro liquid droplets 1 overlap each other. Accordingly, it is not easy to count the number of interference fringes 9 in each of the images a, b, c and d separately from each other. It is also difficult to detect the distributed conditions of micro liquid droplets 1 by determining the center positions of the images a, b, c and d.

Figure 4:
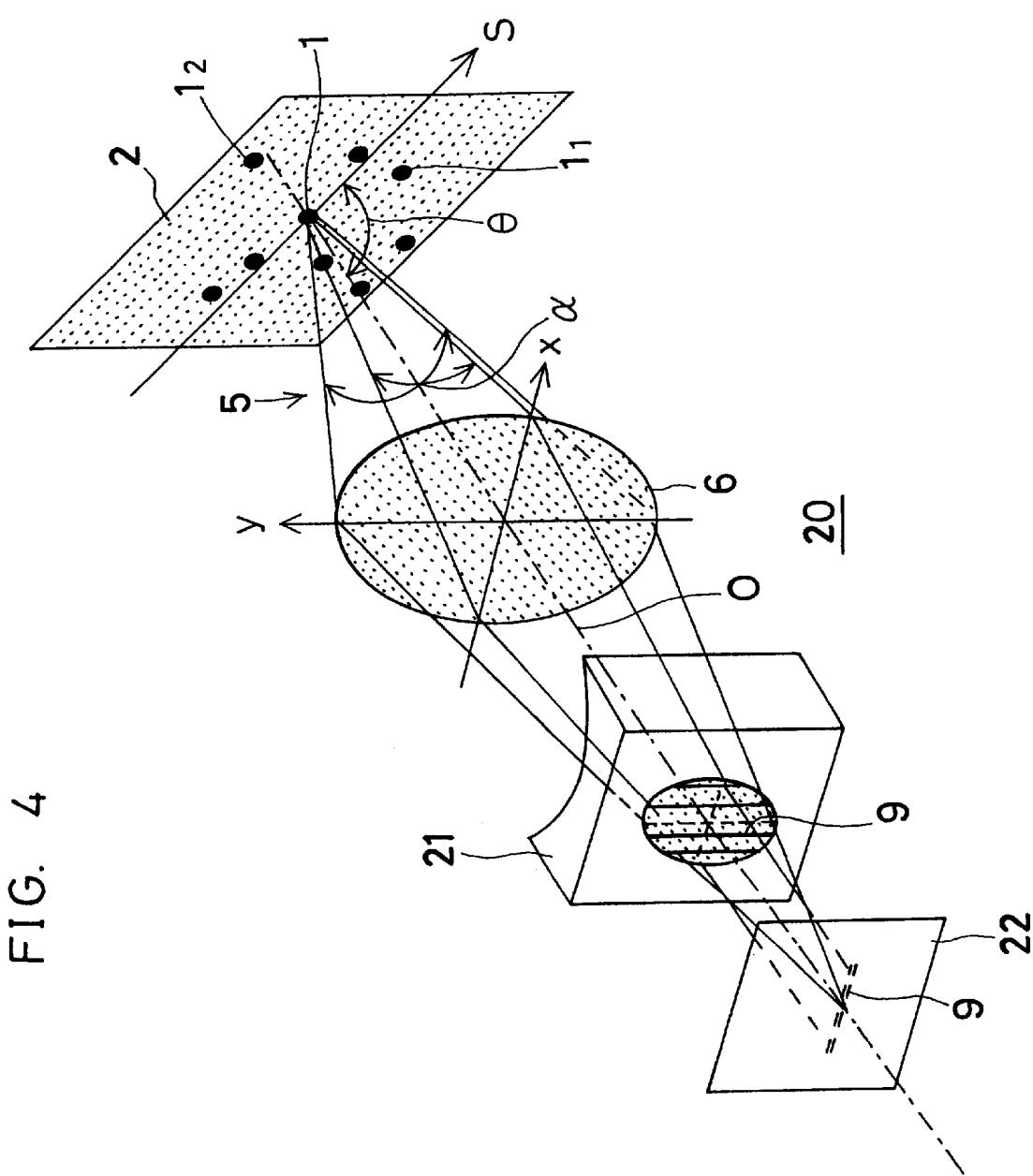
FIG. 4 is a perspective view showing a first embodiment of the optical system for measuring the diameter, distribution and so forth of micro gas bubbles and micro liquid droplets according to the present invention.

Accordingly, an optical system as shown in the perspective view of FIG. 4 is used as a first embodiment of the optical system for measuring the diameter, distribution and so forth of micro gas bubbles and micro liquid droplets according to the present invention. First, let us define a coordinate system. The direction of travel of sheet-shaped parallel illuminating light 2 to be applied to micro liquid droplets 1, $1_1$, $1_2$, ... is denoted by S, and the optical axis of a measuring optical system 20 is denoted by O. The optical axis O is set in a plane perpendicular to the plane of the sheet-shaped parallel light 2. The direction perpendicular to the optical axis O in that plane is defined as an x-axis direction, and the direction perpendicular to both the optical axis O and the x-axis direction and parallel to the sheet-shaped parallel illuminating light 2 is defined as a y-axis direction. The measuring optical system 20 shown in FIG. 4 includes an objective lens 6 and a cylindrical lens 21 (a negative cylindrical lens in the case of FIG. 4) placed in coaxial relation to the objective lens 6 and having a refracting power only in the x-axis direction (having no refracting power in the y-axis direction). An image pickup surface 22 of an image pickup device, e.g. a CCD, is placed in the image-formation plane in the y-axis direction of the measuring optical system 20, that is, in the image-formation plane of the objective lens 6. In contrast, the image-formation plane in the x-axis direction of the measuring optical system 20 is formed at a position off the image pickup surface 22 (behind the image pickup surface 22 in the case of FIG. 4). With this arrangement, the out-of-focus image of the micro liquid droplet 1, which is located in the vicinity of the optical axis O, for example, is circular in the optical path from the objective lens 6, which has a circular aperture, to the cylindrical lens 21. However, as the distance from the cylindrical lens 21 increases toward the image pickup surface 22, the out-of-focus image gradually increases in flatness, and on the image pickup surface 22, the out-of-focus image is a horizontal line. However, there is no change in the number of interference fringes 9 in the out-of-focus image at any position.

Figure 7:
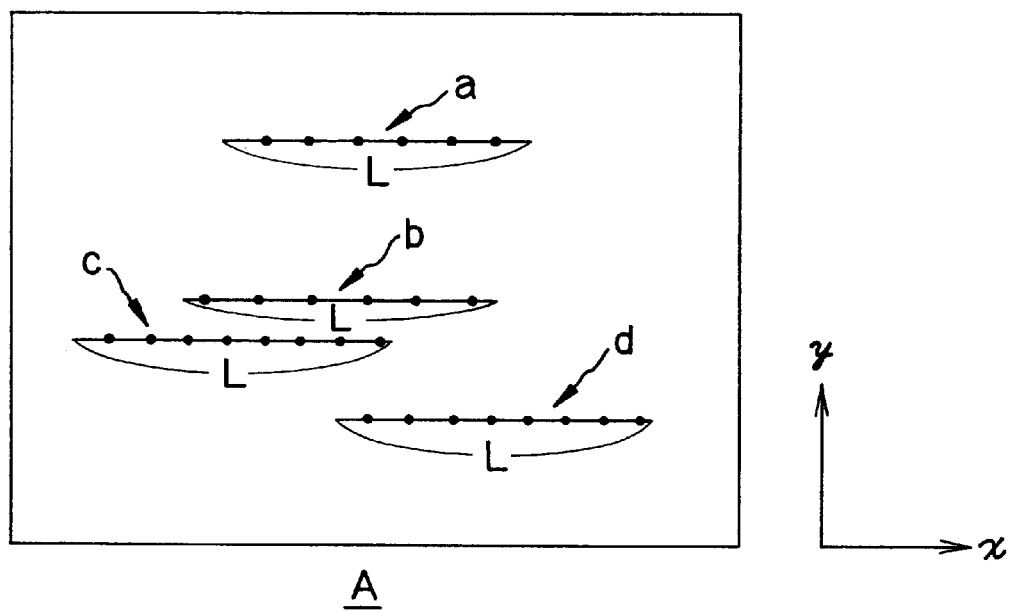
FIG. 7 is a diagram showing out-of-focus images captured with an arrangement as shown in FIG. 4, the out-of-focus images corresponding to those shown in FIG. 6

FIG. 7 shows out-of-focus images a, b, c and d of four micro liquid droplets 1 and so forth obtained from the image pickup surface 22 with the arrangement shown in FIG. 4, which correspond to those in FIG. 6. It should be noted, however, that the each out-of-focus image is illustrated on the assumption that there is no change in the magnifications in the x- and y-axis directions (in reality, because the focal length in the x-axis direction and so forth may change, the magnification of the out-of-focus image may also change).

As will be clear from the comparison of FIGS. 6 and 7, the out-of-focus images a, b, c and d captured with the arrangement shown in FIG. 4 are those which are obtained by compressing the circular out-of-focus images a, b, c and d captured with the arrangement shown in FIG. 1(a) in the vertical direction (y-axis direction) with the center positions thereof left as they are, thereby converting them into one-dimensional images (in the x-axis direction). Accordingly, the four out-of-focus images a, b, c and d no longer overlap each other in the y-axis direction, so that the number of interference fringes 9 in each of the images a, b, c and d can be counted separately with ease. It also becomes easy to determine the center positions of the images a, b, c and d to thereby detect the distributed conditions of the micro liquid droplets 1 and so forth (this will be described later).

It should be noted that the out-of-focus images a, b, c and d as shown in FIG. 6, which are captured by using an axially symmetric measuring optical system, have circular edges around them. Therefore, the diameter of each image can easily be found and it is easy to count the number of interference fringes 9 in the aperture. In the case of the out-of-focus images a, b, c and d compressed as in FIG. 7, however, the light quantity at the center of each image is large. Consequently, the light quantity in the vicinity of each end is relatively small. Accordingly, the ends of the out-of-focus image are inconspicuous, and the length L thereof is unclear. However, if the measuring optical system is under the same conditions and the out-of-focus plane is the same, the length L of any compressed out-of-focus image remains the same. Therefore, there will be no problem in this regard if confirmation is made once in advance under the same conditions.

It should be noted that compressing an out-of-focus image in the vertical direction (y-axis direction) allows an improvement in contrast of the captured out-of-focus image and enables the measurement sensitivity to increase, advantageously.

Incidentally, the lens arrangement of the measuring optical system 20 that produces an in-focus condition in the y-axis direction and an out-of-focus condition in the x-axis direction on the image pickup surface 22 as shown in FIG. 4 may be an anamorphic optical system comprising a combination of an axially symmetric objective lens 6 and a cylindrical lens 21 as stated above, and it may also be an anamorphic optical system using a plane-symmetry anamorphic surface, e.g. a toric surface, as a refracting surface. It is also possible to use an optical system in which the refracting power in the x-axis direction and that in the y-axis direction are the same but the principal plane in the x-axis direction and that in the y-axis direction are different from each other and which is therefore focused on the image pickup surface 22 in the y-axis direction but defocused at the image pickup surface 22 in the x-axis direction. The above-described optical systems may be arranged to include a reflecting surface, as a matter of course.

Figure 5:
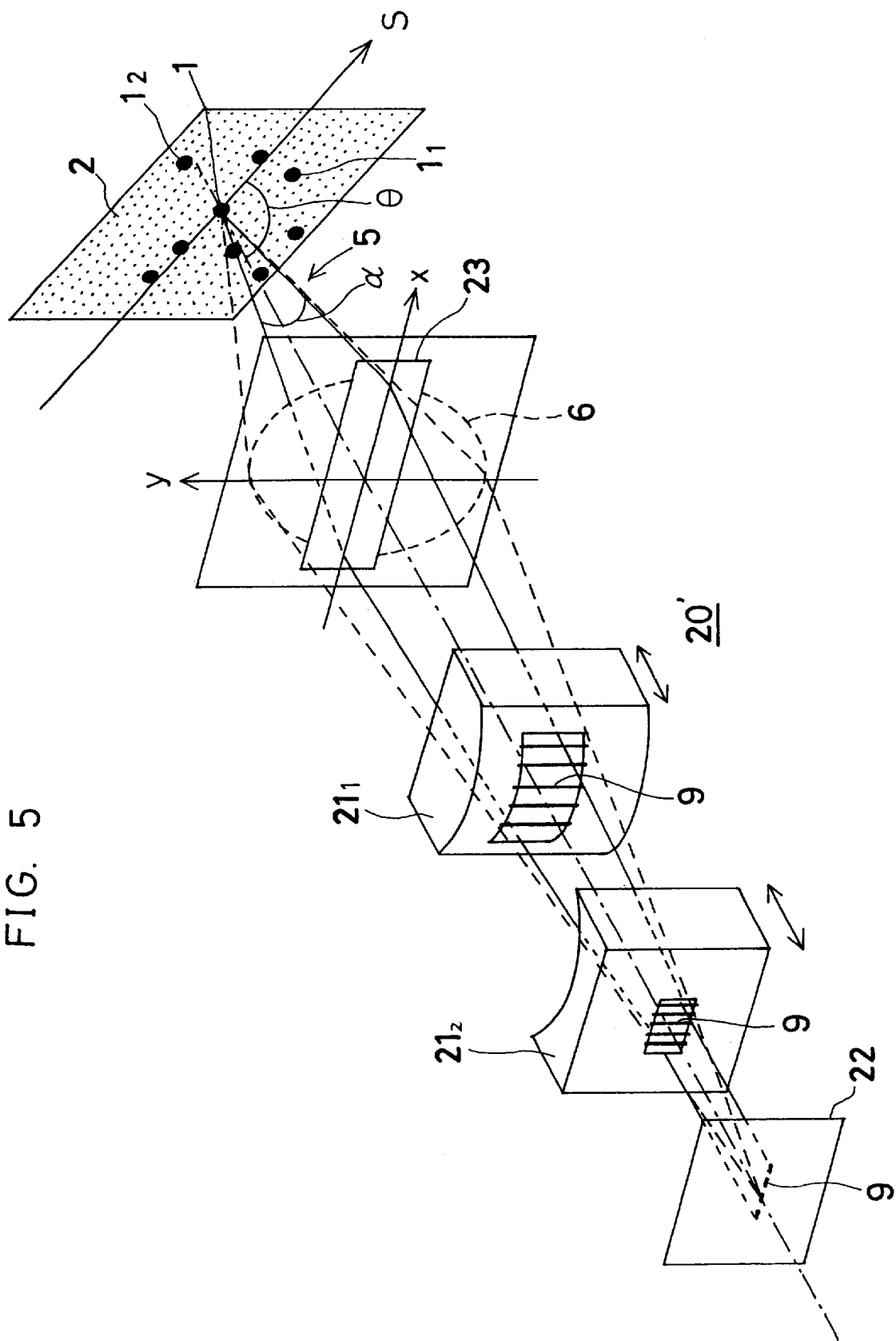
FIG. 5 is a perspective view showing a second embodiment of the optical system for measuring the diameter, distribution and so forth of micro gas bubbles and micro liquid droplets according to the present invention.

FIG. 5 is a perspective view of an optical system for measuring the diameter, distribution and so forth of micro gas bubbles and micro liquid droplets according to a second embodiment of the present invention, which is arranged to further ameliorate unsatisfactory points of the optical system shown in FIG. 4. The measuring optical system 20' comprises an objective lens 6 and a combination of a positive cylindrical lens $21_1$ and a negative cylindrical lens $21_2$ which are placed in coaxial relation to the objective lens 6 and have a refracting power only in the x-axis direction (having no refracting power in the y-axis direction). The position of each of the two cylindrical lenses $21_1$ and $21_2$ is adjustable along the optical axis O. An image pickup surface 22 of an image pickup device is placed in the image-formation plane of the objective lens 6, which is the image-formation plane in the y-axis direction of the measuring optical system 20'.

With the above-described arrangement, the image-formation plane in the x-axis direction of the entire measuring optical system 20' can be adjusted freely with respect to the image pickup surface 22 by adjusting the relative positions of the positive cylindrical lens $21_1$ and the negative cylindrical lens $21_2$ and the position of the combination of these cylindrical lenses relative to the objective lens 6. The focal length of the measuring optical system 20' in the x-axis direction can also be continuously adjusted freely within a certain range. Accordingly, out-of-focus images (FIG. 7) compressed in the vertical direction (y-axis direction) into one-dimensional images (x-axis direction) are captured at the image pickup surface 22 as in the case of FIG. 4. In addition, the length L of each linear out-of-focus image extending in the x-axis direction can be adjusted by adjusting the positions of the two cylindrical lenses $21_1$ and $21_2$.

In the case of FIG. 7, the problem of overlap between the out-of-focus images a, b, c and d in the y-axis direction in FIG. 6 is resolved. However, out-of-focus images located at the same height (the same y-coordinate value) may overlap each other at their edge portions. Therefore, the overlap in the x-axis direction cannot be eliminated with the arrangement shown in FIG. 4. In such a case, if the arrangement shown in FIG. 5 is used, the overlap between the edge portions can be eliminated by making an adjustment so that the length L of each out-of-focus image is shortened. In this case also, there is no change in the number of interference fringes 9 in one out-of-focus image, as has been stated above.

Further, as will be clear from the form of equations (2) and (4), there is a proportional relationship between the number N of interference fringes and the diameter D of a micro liquid droplet (micro gas bubble). Therefore, when the diameter D of each micro liquid droplet 1 under measurement is large, the number of interference fringes 9 in one out-of-focus image is large. Consequently, the interference fringes 9 in the captured image frame may become so fine that it is not easy to count the number of interference fringes 9. In such a case, the positions of the two cylindrical lenses $21_1$ and $21_2$ are adjusted so as to increase the length L of each out-of-focus image in reverse relation to the above, thereby increasing the resolution and thus making it possible to facilitate the counting of interference fringes 9.

Incidentally, in the arrangement shown in FIG. 5, a slit-shaped aperture 23 elongated in the x-axis direction is placed in the vicinity of the objective lens 6 to limit the numerical aperture in the y-axis direction so as to increase the depth of focus (depth of field). As a result, even when the optical axis O of the measuring optical system 20' is at an angle other than 90° with respect to the sheet-shaped parallel illuminating light 2, it is possible to capture and measure an out-of-focus image of a micro liquid droplet $1_1$, for example, which is somewhat away from the optical axis O. It should be noted that because the slit-shaped aperture 23 has a shape elongated in the x-axis direction as stated above, it has no influence on the number of interference fringes at a micro angular spacing $\Delta\theta$ that can be taken in for measurement. Thus, the slit-shaped aperture 23 exerts no influence on the number N of interference fringes in each individual out-of-focus image captured.

Incidentally, as has been suggested above, the angle θ of the optical axis O of the measuring optical system 20 or 20' with respect to the sheet-shaped parallel illuminating light 2 is normally set at an angle between 0° and 90°. In this case, if the principal plane of the objective lens 6 and the image pickup surface 22 are set at right angles to the optical axis O, it is difficult to image all micro liquid droplets in the oblique object plane 2 in the desired state unless the above-described slit-shaped aperture 23 is used. Therefore, a swing & tilt technique is adopted to tilt the principal plane of the objective lens 6 and the image pickup surface 22 with respect to the optical axis O or to move them vertically by combining together shift, tilt and swing as used in photography, thereby allowing all micro liquid droplets in the oblique object plane 2 to be imaged in the desired state. Examples of this technique include a method in which the principal plane of the objective lens 6 and the image pickup surface 22 are tilted with respect to the optical axis O so as to satisfy shine proof conditions.

In the foregoing, the sheet-shaped parallel illuminating light 2 is applied to the measurement space to determine the distribution and diameter of micro liquid droplets or micro gas bubbles located in the illumination sheet plane. However, it is possible to determine the distribution and diameter of micro liquid droplets or micro gas bubbles in a three-dimensional space by moving the sheet-shaped parallel illuminating light 2 in a direction perpendicular to the illumination sheet plane and capturing out-of-focus images at the image pickup surface 22 individually in synchronism with the movement of the sheet-shaped parallel illuminating light 2. In this case, it is preferable to move the image pickup surface 22 in the direction of the optical axis in association with the movement of the sheet-shaped parallel illuminating light 2.

Let us further describe embodiments of a method and apparatus for determining the position, diameter and velocity of micro liquid droplets or micro gas bubbles by using out-of-focus images as shown in FIG. 7, which are captured at the image pickup surface 22 of the above-described measuring optical system 20 according to the present invention.

Figure 8:
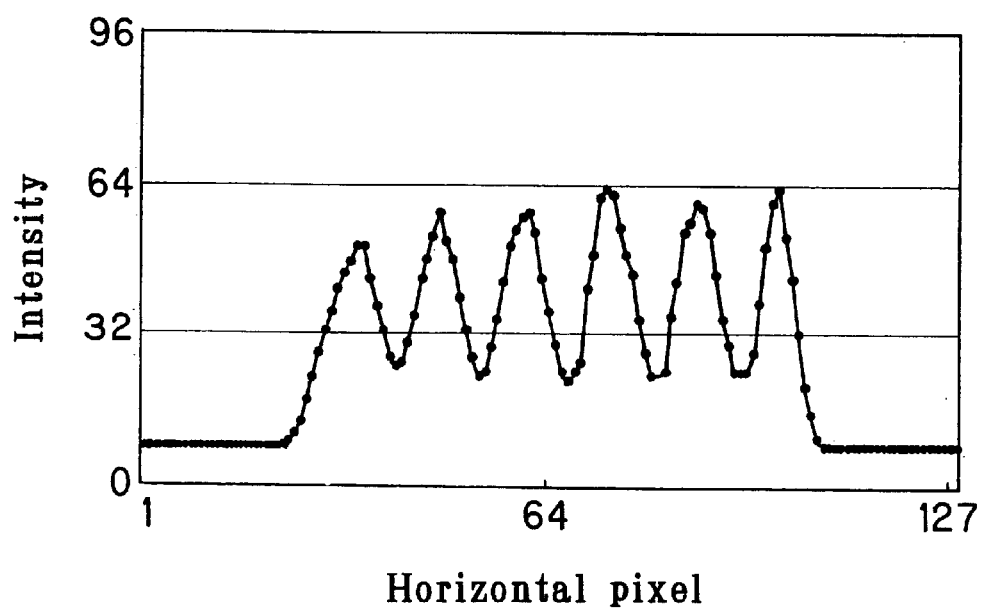
FIG. 8 is a diagram showing an example of an image signal obtained with regard to one interference fringe image.
Figure 9:
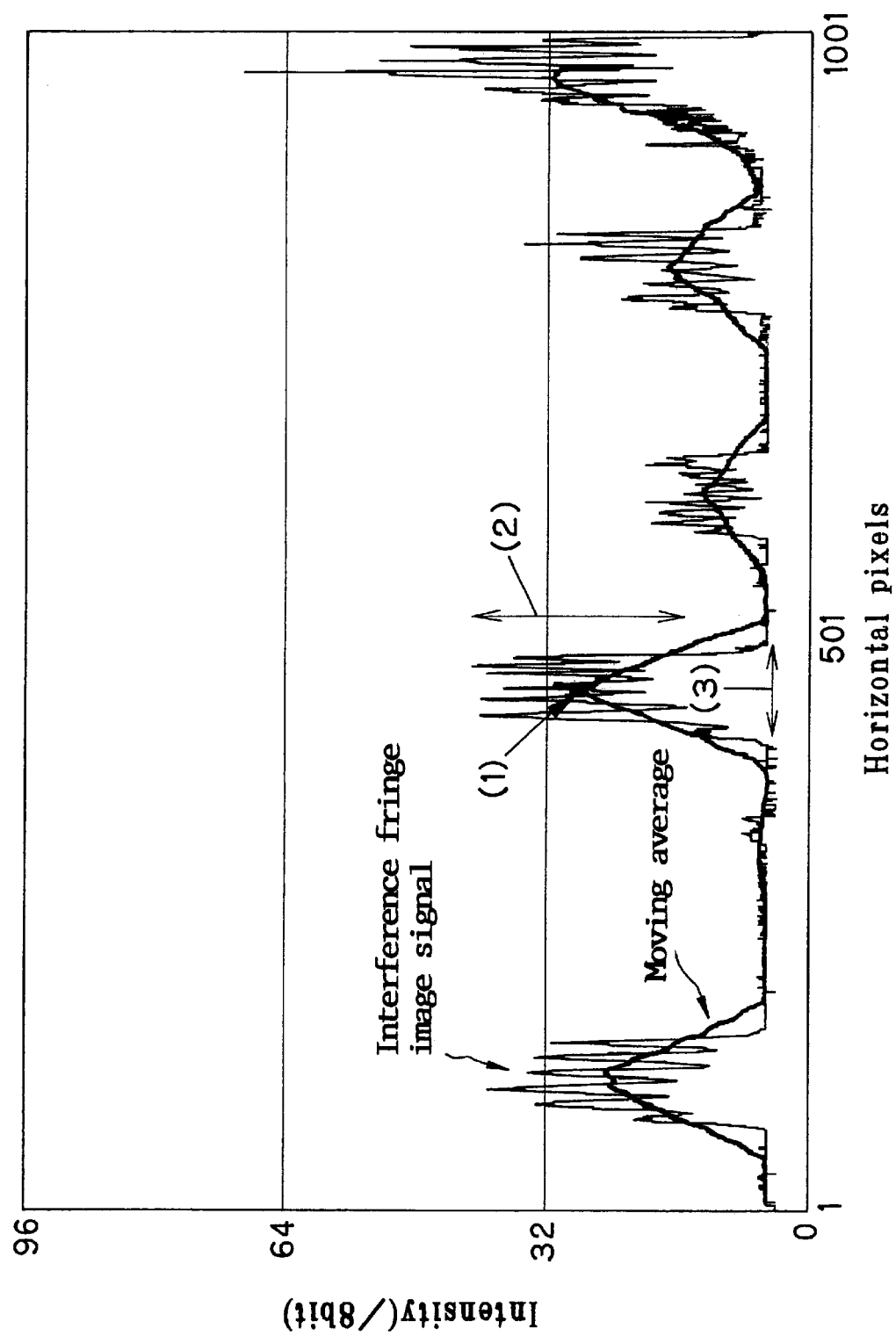
FIG. 9 is a diagram showing image signals of interference fringe images obtained at an image pickup surface and an example of the result of taking moving average.

From the above discussion, the center positions of the linear out-of-focus images a, b, c and d of length L obtained from the image pickup surface 22 approximately correspond to the center positions of the micro liquid droplets $1_1, 1_2, \ldots$ in the sheet-shaped parallel light 2. Therefore, a method of determining the centers of the out-of-focus images (hereinafter referred to as "interference fringe images") a, b, c and d corresponding to the micro liquid droplets will be described first. A captured image frame A as shown in FIG. 7 is horizontally scanned along the lengthwise direction (x-direction) of linear interference fringe images a, b, c and d and vertically scanned in a direction (y-direction) perpendicular to the lengthwise direction, thereby obtaining an image signal for the whole captured image frame A. The image signal contains a signal corresponding to each of the interference fringe images a, b, c and d as shown in FIG. 8 by way of example. The signal has a length L in terms of distance and has peaks corresponding to the number N of interference fringes therein. Such signals are present in correspondence to the respective positions of the interference fringe images a, b, c and d. In FIG. 8, the abscissa axis corresponds to the position in the longitudinal direction of the interference fringe image (expressed in pixels), and the ordinate axis corresponds to the signal intensity. To determine the center position of a single interference fringe image as shown in FIG. 8, moving average should be taken along the longitudinal direction of the interference fringe image. The length L of one interference fringe image is determined by the condition of the measuring optical system 20 and the position of the image pickup surface 22. Therefore, the average is taken in the range extending from a distance L/2 forward of a specific position to a distance L/2 rearward of the specific position and determined to be a value at this position, and the specific position is moved successively to obtain a moving average value. FIG. 9 shows the image signals of the interference fringe images obtained at the image pickup surface 22 and an example of the result of taking moving average as stated above. When moving average is taken, an approximately triangular-wave signal is obtained as illustrated in the figure. The peak position (1) of the signal is the center position of the interference fringe image corresponding to a micro liquid droplet. It should be noted that the range (3) in FIG. 9 corresponds to the length L of the interference fringe image.

Incidentally, a signal longer than the length L of the signal of an interference fringe image may appear in the signal in the same horizontal scanning direction. This occurs in some rare cases where a plurality of interference fringe images superimposed on one another are present in the same horizontal scanning direction. In this case, the half-width of the image signal of the interference fringe image or the half-width of the moving average signal becomes longer than in normal cases. Therefore, the situation can be readily judged. In such a case, no problem arises even if the image signal of the interference fringe image is removed. It is also possible to determine the centers of two interference fringe images from the half-width.

It should be noted that because a noise may be mixed in the image signal, it is desirable to judge that an interference fringe image is present only when it is decided that the amplitude (2) of the high-frequency component in FIG. 9 is more than a predetermined value.

Thus, the position of each micro liquid droplet in the captured image frame A is determined, and the micro liquid droplet distribution and density in the space are determined.

Next, a method of determining the diameter of each micro liquid droplet will be described. As has been stated above, because the length of a signal indicating each interference fringe image in the image signal obtained by scanning the captured image frame A is L, the range extending from L/2 forward of the center position determined as stated above to L/2 rearward of the center position corresponds to the signal of each interference fringe image. Therefore, a signal extending over the range of L/2 forward of the determined center of the interference fringe image to L/2 rearward of it, that is, a signal having a length L in the longitudinal direction and centered at the center position of the interference fringe image, is cut out, and the absolute value or square (power spectrum) of Fourier transform of the cut-out signal is determined, thereby obtaining the frequency f of the interference fringe image. By multiplying the frequency f by the length L of the interference fringe image, the number N of interference fringes in the out-of-focus image is obtained. Thereafter, N is substituted into equation (2) or (4) to obtain the diameter D of the micro liquid droplet or the micro gas bubble.

Figure 11:
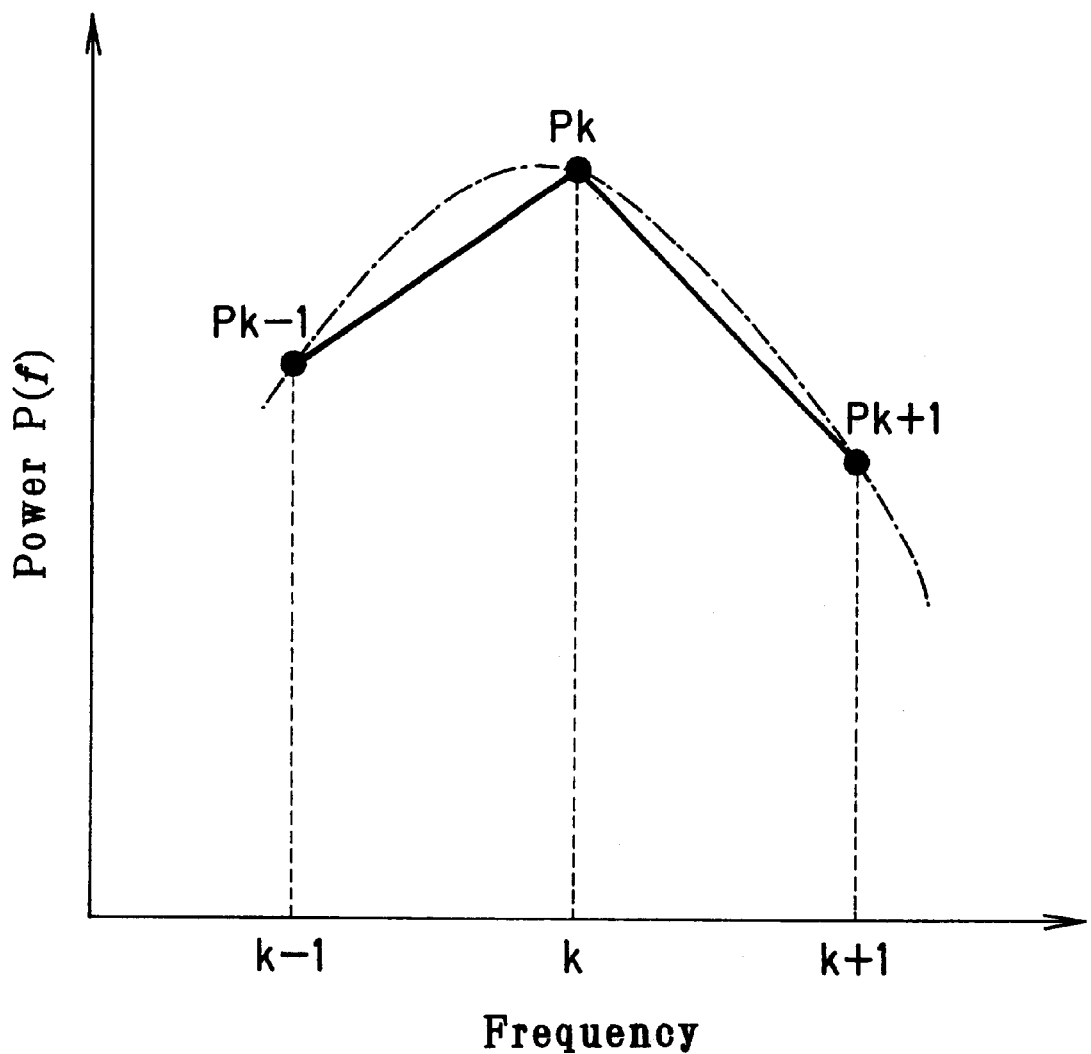
FIG. 11 is a diagram for explaining a method of accurately obtaining the frequency of the original signal from a discrete power spectrum by function fitting.

To Fourier-transform the signal of length L and determine the frequency f from the power spectrum, actually, the signal is multiplied by a Hanning window function, for example, as a window function for eliminating the influence of the edge, thereby performing fast Fourier transform (FFT). Incidentally, FFT is a kind of discrete Fourier transform. In discrete Fourier transform, the frequency interval obtained is $1/M\Delta$, where $\Delta$ is the sampling interval for a signal to be transformed and M is the sampling number. Accordingly, frequency can be obtained only at discrete frequency positions. If the frequency of the interference fringe image is precisely coincident with any one of the frequencies discrete at a frequency interval $1/M\Delta$, the Fourier-transformed frequency signal appears as a single peak at the frequency position. However, when the frequency of the interference fringe image is present between two adjacent discrete frequencies, the signal undesirably appears not only at the positions of the two adjacent frequencies but also at the positions of discrete frequencies around them. An example of this is shown in FIG. 10. FIG. 10(a) shows a signal of an interference fringe image. FIG. 10(b) shows a power spectrum obtained by multiplying the signal by a Hanning window function and performing FFT. As will be clear from FIG. 10(b), a peak $P_k$ is present at the position of a frequency k, and signals $P_{k-1}$ and $P_{k+1}$ are also present at the positions of discrete frequencies k−1 and k+1 on both sides of the frequency k. There are also signals on both sides of these signals. To accurately obtain the frequency of the original signal by function fitting from such a discrete power spectrum, methods using various fitting functions are available. However, the frequency of the original signal can be accurately obtained by a method using a Gaussian function (R. J. Adrian, et al. "Applications of Laser Techniques to Fluid Mechanics 5th International Symposium Lisbon, Portugal, Jul. 9–12, 1990" pp. 268–287 (Springer-Verlag)) . That is, as shown in FIG. 11, when a peak $P_k$ is present at the position of a discrete frequency k and signals $P_{k-1}$ and $P_{k+1}$ smaller than the peak $P_k$ are also present at the positions of discrete frequencies k−1 and k+1 on both sides of the peak $P_k$, the frequency f of the original signal can be obtained without considering signals at other frequencies as follows:

$$f=f_k+\tfrac{1}{2}\times\{(\log P_{k-1}-\log P_{k+1})\div(\log P_{k-1}-2\log P_k+\log P_{k+1})\} \quad (5)$$

As the above-described window function and fitting function, other publicly known functions are also usable, as a matter of course.

Next, a method of determining the velocity (vector) of each micro liquid droplet will be described. In this case, image frames A and A' as shown in FIG. 7 are captured at a micro time interval $\Delta t$. Assuming that the two captured image frames A and A' are those which are schematically shown in FIGS. 12(a) and (b), interference fringe images a, b, c and d in each of the captured image frames A and A' change as illustrated in the figures. Therefore, the cross correlation between the interference fringe images a, b, c and d in the two capture image frames A and A' is calculated to determine the displacement $\Delta s_i$ of each interference fringe image in the form of a vector. The displacement distribution is schematically shown in FIG. 12(c).

From the displacement $\Delta s_i$ thus determined, the velocity $u_i$ of each micro liquid droplet is determined as follows:

$$u_i=\Delta s_i/\Delta t \quad (6)$$

More specifically, sheet-shaped parallel illuminating light 2 (FIGS. 4 or 5) is applied at a micro time interval $\Delta t$ by using a double-pulsed laser, for example, and two images A and A' are captured at the image pickup surface 22 synchronously with the emission of the light. Signals of interference fringe images are cut out from the images A and A'. The method of cutting out signals is the same as the above-described method of determining the frequency. In this case, however, not only a signal from a single scanning line but also signals from adjacent scanning lines perpendicularly intersecting the interference fringe image are cut out at the same time, and the cross correlation is calculated for each interference fringe image cut out from the images A and A'. In the calculation of the cross correlation, each interference fringe image cut out from the two images is shifted by one pixel at a time in the x- and y-directions to calculate a correlation value. The upper limit of the displacement for correlation calculation in the x- and y-directions is set appropriately in advance. The displacement of the vector to a position (peak position) where the highest correlation value is obtained is determined to be displacement $\Delta s_i$ for each interference fringe image.

In the above-described calculation, each cut-out interference fringe image includes the interference fringe signal, and the interference fringes may move leftward or rightward in the interference fringe image according to the phase. Therefore, the displacement of the interference fringe image obtained from the above-described cross correlation is not always the same as the actual displacement of the interference fringe image. Accordingly, if the cross correlation is calculated with respect to the interference fringe image in the state of including the interference fringe signal as stated above, it is not always possible to obtain an accurate displacement of the interference fringe image. Therefore, it is desirable to remove the high-frequency component from the interference fringe signal by passing the interference fringe image signal through a low-pass filter before the cross correlation is calculated.

Further, because the calculation of the cross correlation is also performed in units of one pixel, an displacement $\Delta s_i$ in subpixel units cannot directly be obtained. A peak position expressed in subpixel units can be accurately obtained by applying various functions to discrete cross-correlation values obtained in the x- and y-directions (e.g. a Gaussian function or a quadratic function may be used; however, a sine function or a cosine function is preferably used because the cross correlation with a sine function is calculated in the present invention).

It should be noted, however, that the displacement $\Delta s_i$ obtained by the above-described technique does not always accurately correspond to the displacement of a micro liquid droplet between different instances in time. Therefore, it is desirable to judge whether or not the displacement $\Delta s_i$ accurately correspond as follows. The frequency in the cut-out signal of each interference fringe image is determined as stated above, and it is judged whether or not the frequency has changed. Alternatively, it is judged whether or not the rate of change due to evaporation or condensation is less than a predetermined value. Only when the rate of change is less than the predetermined value, it is judged that the displacement $\Delta s_i$ accurately corresponds to the displacement of the micro liquid droplet.

Figure 13:
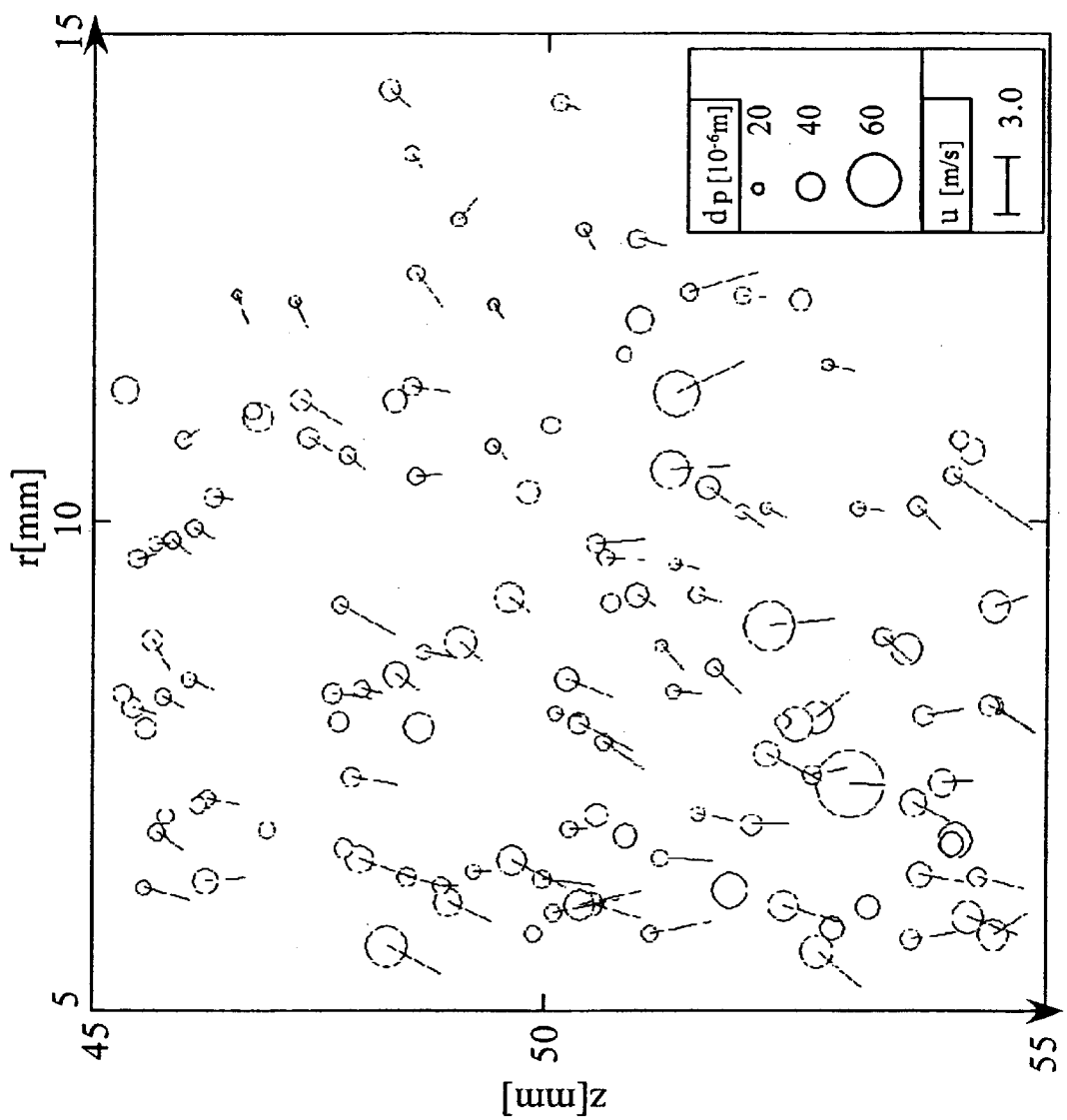
FIG. 13 is a diagram showing an example of an image frame displaying the position, diameter and velocity distributions of micro liquid droplets or micro gas bubbles measured simultaneously.

FIG. 13 shows an example of an image frame displaying the position, diameter and velocity distributions of micro liquid droplets or micro gas bubbles simultaneously measured as stated above. The center of each circle indicates position. The size of each circle indicates diameter. The line segment indicates velocity.

It should be noted that an apparatus for carrying out the above-described method of determining the position, diameter and velocity of micro liquid droplets or micro gas bubbles using out-of-focus images can be readily implemented via software using a personal computer.

Although the method and apparatus for measuring the diameter, distribution and so forth of micro gas bubbles and micro liquid droplets, together with the optical system for measuring the diameter, distribution and so forth of micro gas bubbles and micro liquid droplets, according to the present invention have been described above on the basis of embodiments, the present invention is not limited to these embodiments but can be modified in a variety of ways.

INDUSTRIAL APPLICABILITY

As will be clear from the foregoing description, the method and apparatus for measuring the diameter, distribution and so forth of micro gas bubbles and micro liquid droplets, together with the optical system for measuring the diameter, distribution and so forth of micro gas bubbles and micro liquid droplets, according to the present invention are arranged to capture out-of-focus images of micro gas bubbles or micro liquid droplets with an imaging optical system at an imaging plane where the images are out of focus in a direction parallel to a plane containing the direction of travel of a sheet-shaped parallel laser beam and the optical axis of the imaging optical system and where the images are substantially in focus in a direction perpendicular to the plane. Consequently, the out-of-focus image corresponding to each micro gas bubble or micro liquid droplet becomes a one-dimensional image compressed in the direction perpendicular to the plane. Therefore, even when the spatial distribution density of micro gas bubbles and micro liquid droplets is high, the respective out-of-focus images can be separated from each other. Accordingly, the number of interference fringes in each out-of-focus image can be readily counted separately from each other. In addition, it becomes easy to determine the center position of each out-of-focus image to detect the distributed conditions of micro gas bubbles or micro liquid droplets. Even in such a case, the position, diameter and velocity distributions of micro gas bubbles and micro liquid droplets can be measured simultaneously and accurately.

What is claimed is:

1. A method of measuring a diameter, distribution and so forth of micro gas bubbles, said method comprising the steps of:

applying a sheet-shaped parallel laser beam to a liquid space in which micro gas bubbles are floating;

capturing out-of-focus images of micro gas bubbles irradiated with the laser beam from a lateral direction which is at an angle θ to a direction of travel of the laser beam;

measuring the number N of interference fringes in the out-of-focus image corresponding to each micro gas bubble; and determining a diameter D of the micro gas bubble from the following relationship:

$$D=(2\lambda N/n\alpha)[\cos(\theta/2)-\sin(\theta/2)+\sqrt{\{n^2+1-2n\cos(\theta/2)\}}]^{-1} \quad (4)$$

where λ is a wavelength of the laser beam; α is an angle subtended at the micro gas bubble by an objective lens used to capture the image of the micro gas bubble; and n is a relative index of refraction of a liquid in which the micro gas bubble is present.

2. A method of measuring a diameter, distribution and so forth of micro gas bubbles and micro liquid droplets, said method comprising the steps of:

applying a sheet-shaped parallel laser beam to a space in which micro gas bubbles or micro liquid droplets are floating;

capturing out-of-focus images of micro gas bubbles or micro liquid droplets irradiated with the laser beam from a lateral direction which is at a predetermined angle to a direction of travel of the laser beam; and measuring numbers of interference fringes in the respective out-of-focus images corresponding to the micro gas bubbles or the micro liquid droplets to determine diameters and distribution of the micro gas bubbles or the micro liquid droplets;

wherein said out-of-focus images are captured with an imaging optical system at an imaging plane where the images are out of focus in a direction parallel to a plane containing the direction of travel of said sheet-shaped parallel laser beam and an optical axis of the imaging optical system and where the images are substantially in focus in a direction perpendicular to said plane.

3. A method of measuring a diameter, distribution and so forth of micro gas bubbles and micro liquid droplets according to claim 2, wherein a spacing of interference fringes on the imaging plane is adjustable by adjusting a defocus condition of said out-of-focus images.

4. A method of measuring a diameter, distribution and so forth of micro gas bubbles and micro liquid droplets according to claim 2 or 3, wherein said sheet-shaped parallel laser beam is moved in parallel to a direction perpendicular to a plane of said sheet-shaped parallel laser beam with respect to the space in which micro gas bubbles or micro liquid droplets are floating, and said out-of-focus images are captured in synchronism with movement of said sheet-shaped parallel laser beam.

5. A method of measuring a diameter, distribution and so forth of micro gas bubbles and micro liquid droplets, said method comprising the steps of:

applying a sheet-shaped parallel laser beam to a space in which micro gas bubbles or micro liquid droplets are floating;

capturing linear out-of-focus images of micro gas bubbles or micro liquid droplets irradiated with the laser beam from a lateral direction which is at a predetermined angle to a direction of travel of the laser beam with an imaging optical system at an imaging plane where the images are out of focus in a direction parallel to a plane containing the direction of travel of said laser beam and an optical axis of the imaging optical system and where the images are substantially in focus in a direction perpendicular to said plane, said linear out-of-focus images extending in a direction of said plane in correspondence to the micro gas bubbles or the micro liquid droplets; and determining a center of each of said out-of-focus images, thereby determining a center position of the corresponding micro gas bubble or micro liquid droplet.

6. A method of measuring a diameter, distribution and so forth of micro gas bubbles and micro liquid droplets according to claim 5, wherein said center position is determined from a peak position of a moving average value obtained by taking an average in a range extending from a distance L/2 forward of a specific position to a distance L/2 rearward of the specific position in a longitudinal direction and determining the average to be a value at this position, where L is a length of a linear out-of-focus image, and successively moving the specific position.

7. A method of measuring a diameter, distribution and so forth of micro gas bubbles and micro liquid droplets, said method comprising the steps of:

applying a sheet-shaped parallel laser beam to a space in which micro gas bubbles or micro liquid droplets are floating;

capturing linear out-of-focus images of micro gas bubbles or micro liquid droplets irradiated with the laser beam from a lateral direction which is at a predetermined angle to a direction of travel of the laser beam with an imaging optical system at an imaging plane where the images are out of focus in a direction parallel to a plane containing the direction of travel of said laser beam and an optical axis of the imaging optical system and where the images are substantially in focus in a direction perpendicular to said plane, said linear out-of-focus images extending in a direction of said plane in correspondence to the micro gas bubbles or the micro liquid droplets;

subjecting each of the out-of-focus images to Fourier transform to obtain a frequency;

multiplying the obtained frequency by a length of the out-of-focus image to obtain the number of interference fringes in the out-of-focus image; and determining a diameter of the micro gas bubble or the micro liquid droplet on a basis of the number of interference fringes.

8. A method of measuring a diameter, distribution and so forth of micro gas bubbles and micro liquid droplets according to claim 7, wherein discrete Fourier transform is performed as said Fourier transform to obtain a discrete frequency distribution, and function fitting is applied to the discrete frequency distribution to obtain a diameter of the micro gas bubble or the micro liquid droplet.

9. A method of measuring a diameter, distribution and so forth of micro gas bubbles and micro liquid droplets, said method comprising the steps of:

applying a sheet-shaped parallel laser beam to a space in which micro gas bubbles or micro liquid droplets are floating;

capturing two image frames at a micro time interval $\Delta t$, the two image frames each containing linear out-of-focus images of micro gas bubbles or micro liquid droplets irradiated with the laser beam, the linear out-of-focus images being captured from a lateral direction which is at a predetermined angle to a direction of travel of the laser beam with an imaging optical system at an imaging plane where the images are out of focus in a direction parallel to a plane containing the direction of travel of said laser beam and an optical axis of the imaging optical system and where the images are substantially in focus in a direction perpendicular to said plane, said linear out-of-focus images extending in a direction of said plane in correspondence to the micro gas bubbles or the micro liquid droplets;

calculating cross correlation between the two captured image frames for each linear out-of-focus image in the two captured image frames to obtain a displacement $\Delta s_i$ of each linear out-of-focus image; and determining a velocity $u_i$ of each micro gas bubble or micro liquid droplet from the following relationship:

$$u_i = \Delta s_i / \Delta t \qquad (6).$$

10. A method of measuring a diameter, distribution and so forth of micro gas bubbles and micro liquid droplets according to claim 9, wherein when cross correlation is calculated between said two captured image frames, a high-frequency component corresponding to interference fringes in the linear out-of-focus image is removed.

11. A method of measuring a diameter, distribution and so forth of micro gas bubbles and micro liquid droplets, said method comprising the steps of:

applying a sheet-shaped parallel laser beam to a space in which micro gas bubbles or micro liquid droplets are floating;

capturing linear out-of-focus images of micro gas bubbles or micro liquid droplets irradiated with the laser beam from a lateral direction which is at a predetermined angle to a direction of travel of the laser beam with an imaging optical system at an imaging plane where the images are out of focus in a direction parallel to a plane containing the direction of travel of said laser beam and an optical axis of the imaging optical system and where the images are substantially in focus in a direction perpendicular to said plane, said linear out-of-focus images extending in a direction of said plane in correspondence to the micro gas bubbles or the micro liquid droplets;

determining a center of each of said out-of-focus images, thereby determining a center position of the corresponding micro gas bubble or micro liquid droplet;

subjecting each of the out-of-focus images to Fourier transform to obtain a frequency;

multiplying the obtained frequency by a length of the out-of-focus image to obtain the number of interference fringes in the out-of-focus image;

determining a diameter of the micro gas bubble or the micro liquid droplet on a basis of the number of interference fringes;

capturing two image frames containing the linear out-of-focus images at a micro time interval $\Delta t$;

calculating cross correlation between the two captured image frames for each linear out-of-focus image in the two captured image frames to obtain a displacement $\Delta s_i$ of each linear out-of-focus image; and determining a velocity $u_i$ of each micro gas bubble or micro liquid droplet from the following relationship:

$$u_i = \Delta s_i / \Delta t \qquad (6).$$

12. An apparatus for measuring a diameter, distribution and so forth of micro gas bubbles and micro liquid droplets, said apparatus comprising:

laser beam application means for applying a sheet-shaped parallel laser beam to a space in which micro gas bubbles or micro liquid droplets are floating;

imaging means for capturing linear out-of-focus images of micro gas bubbles or micro liquid droplets irradiated with the laser beam, which is applied by said laser beam application means, from a lateral direction which is at a predetermined angle to a direction of travel of the laser beam with an imaging optical system at an imaging plane where the images are out of focus in a direction parallel to a plane containing the direction of travel of said laser beam and an optical axis of the imaging optical system and where the images are substantially in focus in a direction perpendicular to said plane, said linear out-of-focus images extending in a direction of said plane in correspondence to the micro gas bubbles or the micro liquid droplets;

center position measuring means for determining a center of each of said out-of-focus images to thereby determine a center position of the corresponding micro gas bubble or micro liquid droplet;

diameter measuring means for subjecting each of the out-of-focus images to Fourier transform to obtain a frequency, multiplying the obtained frequency by a length of the out-of-focus image to obtain the number of interference fringes in the out-of-focus image, and determining a diameter of the micro gas bubble or the micro liquid droplet on a basis of the number of interference fringes; and velocity measuring means for capturing two image frames containing the linear out-of-focus images at a micro time interval Δt, calculating cross correlation between the two captured image frames for each linear out-of-focus image in the two captured image frames to obtain a displacement $\Delta s_i$ of each linear out-of-focus image, and determining a velocity $u_i$ of each micro gas bubble or micro liquid droplet from the following relationship:

$$u_i = \Delta s_i / \Delta t \tag{6}$$

13. An optical system for measuring a diameter, distribution and so forth of micro gas bubbles and micro liquid droplets by applying a sheet-shaped parallel laser beam to a space in which micro gas bubbles or micro liquid droplets are floating, capturing out-of-focus images of micro gas bubbles or micro liquid droplets irradiated with the laser beam from a lateral direction which is at a predetermined angle to a direction of travel of the laser beam, and measuring numbers of interference fringes in the respective out-of-focus images corresponding to the micro gas bubbles or the micro liquid droplets to determine diameters and distribution of the micro gas bubbles or the micro liquid droplets, said optical system comprising:

an imaging optical system in which a focal length or an image-side principal plane in a direction parallel to a plane containing the direction of travel of said sheet-shaped parallel laser beam and an optical axis of the imaging optical system and a focal length or an image-side principal plane in a direction perpendicular to said plane containing the optical axis of the imaging optical system are different from each other; and image pickup means placed in an image plane which is in a vicinity of an image-formation plane in the direction perpendicular to said plane and which is off an image-formation plane in the direction parallel to said plane.

14. An optical system for measuring a diameter, distribution and so forth of micro gas bubbles and micro liquid droplets according to claim 13, wherein said imaging optical system is an anamorphic optical system comprising a combination of an axially symmetric objective lens and a cylindrical lens.

15. An optical system for measuring a diameter, distribution and so forth of micro gas bubbles and micro liquid droplets according to claim 13 or 14, wherein at least one of the focal length and the image-side principal plane of said imaging optical system in the direction parallel to said plane is adjustable.

16. An optical system for measuring a diameter, distribution and so forth of micro gas bubbles and micro liquid droplets according to any one of claims 12 to 14, wherein said imaging optical system has a rectangular aperture elongated in the direction parallel to said plane.

* * * * *